(12) United States Patent
Yamaguchi et al.

(10) Patent No.: US 9,167,960 B2
(45) Date of Patent: Oct. 27, 2015

(54) ENDOSCOPE SYSTEM, PROCESSOR DEVICE THEREOF, AND IMAGE PRODUCING METHOD

(71) Applicant: FUJIFILM Corporation, Tokyo (JP)

(72) Inventors: Hiroshi Yamaguchi, Ashigarakami-gun (JP); Takaaki Saito, Ashigarakami-gun (KP); Takayuki Iida, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 277 days.

(21) Appl. No.: 13/746,880

(22) Filed: Jan. 22, 2013

(65) Prior Publication Data

US 2013/0211217 A1   Aug. 15, 2013

(30) Foreign Application Priority Data

Feb. 14, 2012   (JP) ................................ 2012-029749

(51) Int. Cl.
| | |
|---|---|
| A61B 1/06 | (2006.01) |
| A61B 5/1459 | (2006.01) |
| A61B 5/1455 | (2006.01) |
| A61B 5/00 | (2006.01) |
| A61B 1/04 | (2006.01) |
| A61B 1/00 | (2006.01) |
| A61B 1/005 | (2006.01) |
| A61B 5/145 | (2006.01) |

(52) U.S. Cl.
CPC ........... *A61B 1/0638* (2013.01); *A61B 1/00009* (2013.01); *A61B 1/00039* (2013.01); *A61B 1/00045* (2013.01); *A61B 1/0052* (2013.01); *A61B 1/04* (2013.01); *A61B 5/1459* (2013.01); *A61B 5/14546* (2013.01); *A61B 5/14551* (2013.01); *A61B 5/7278* (2013.01); *A61B 5/742* (2013.01); *A61B 1/0005* (2013.01); *A61B 1/0646* (2013.01); *A61B 1/0653* (2013.01); *A61B 2562/046* (2013.01)

(58) Field of Classification Search
None
See application file for complete search history.

(56) References Cited

U.S. PATENT DOCUMENTS

| | | | | |
|---|---|---|---|---|
| 5,001,556 | A | * | 3/1991 | Nakamura et al. ............... 348/70 |
| 5,408,998 | A | * | 4/1995 | Mersch ......................... 600/334 |
| 5,515,449 | A | | 5/1996 | Tsuruoka et al. |
| 2009/0247881 | A1 | * | 10/2009 | Maeda et al. .................. 600/476 |
| 2009/0312607 | A1 | * | 12/2009 | Sunagawa et al. ............. 600/160 |
| 2011/0237884 | A1 | * | 9/2011 | Saito ............................. 600/109 |

FOREIGN PATENT DOCUMENTS

| | | |
|---|---|---|
| EP | 2368480 A1 | 9/2011 |
| JP | 2011-194151 A | 10/2011 |

* cited by examiner

*Primary Examiner* — Long V Le
*Assistant Examiner* — Marjan Saboktakin
(74) *Attorney, Agent, or Firm* — Birch, Stewart, Kolasch & Birch, LLP

(57) ABSTRACT

First and second white light is generated by excitations of phosphors with first and second laser beams having center wavelengths of 473 nm and 445 nm, respectively. The first and second white light is applied, in respective frames, sequentially to a region of interest in a subject. A color image sensor images the region of interest in the each frame. Based on a shift amount, calculated from green signals of first and second frames, between images, an image of a blue signal of the first frame is moved to be aligned with an image of a green signal and an image of a red signal of the second frame. After the alignment, an oxygen saturation image representing an oxygen saturation level of hemoglobin in blood is produced from the blue signal of the first frame and green and red signals of the second frame.

10 Claims, 16 Drawing Sheets

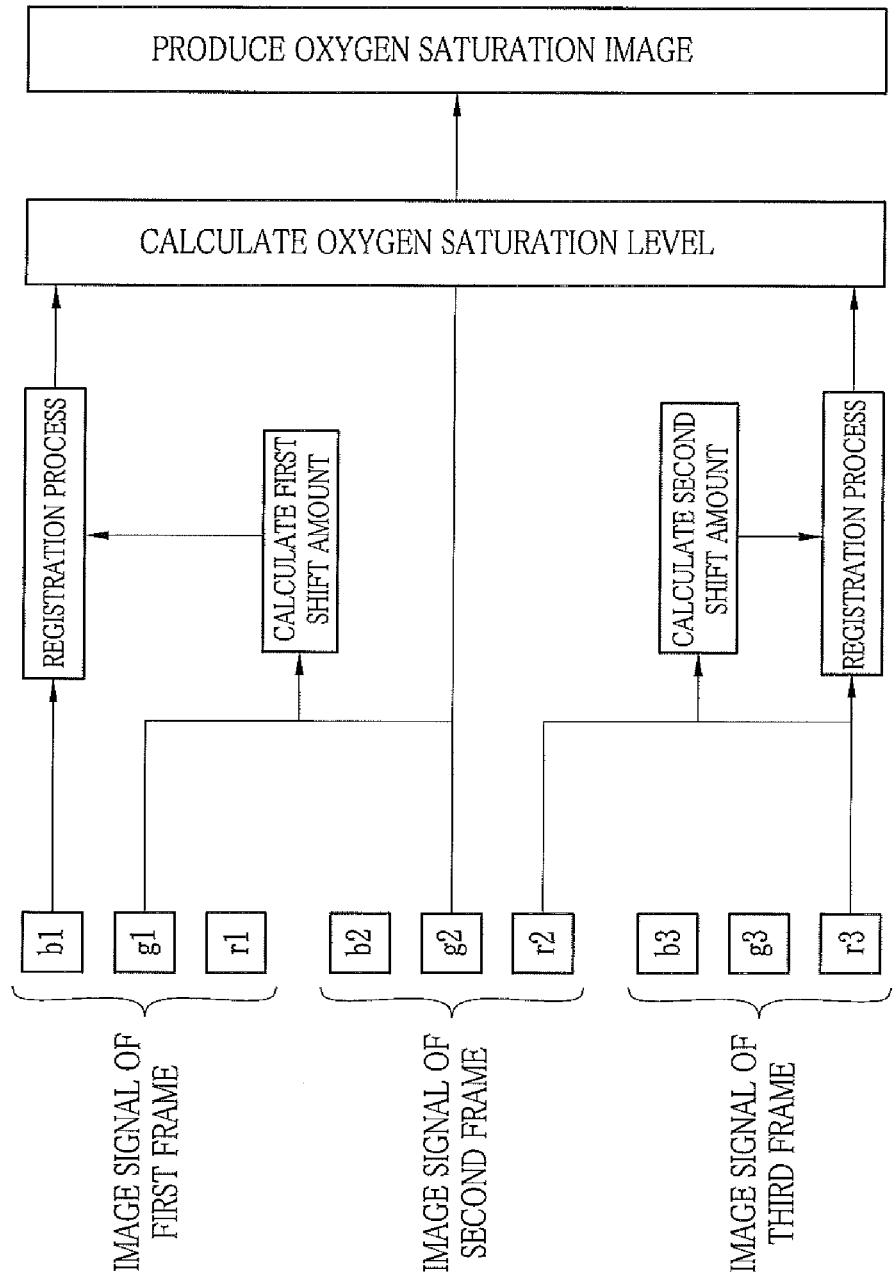

ENDOSCOPE SYSTEM, PROCESSOR DEVICE THEREOF, AND IMAGE PRODUCING METHOD

BACKGROUND OF THE INVENTION

1. Field of the invention

The present invention relates to an endoscope system for applying two or more types of color light sequentially and calculating an oxygen saturation level of hemoglobin in blood and imaging an oxygen saturation level calculated, a processor device for an endoscope system, and an image producing method.

2. Description Related to the Prior Art

Recently in the medical field, diagnoses using endoscope systems have been common. The endoscope system is composed of a light source device, a processor device, and an endoscope device. Normal observation and special observation using the endoscope system are known. In the normal observation, broadband light, for example, white light is used to illuminate a region of interest in a subject. This is effective in observing the region of interest as a whole. In the special observation, the illumination light of particular wavelength(s) is used in accordance with the purpose of the observation.

In the normal observation, the broadband light such as xenon light from the light source device is applied to the region of interest through a lighting section of the endoscope device. A reflection image is imaged with a color image sensor. An image signal acquired is sent to the processor device. Thereby, a color normal image is displayed on a monitor of the processor device.

In the special observation, a blood vessel emphasized image and an oxygen saturation image are observed. This enables finding cancer which is difficult to find in the normal observation. To observe the blood vessel emphasized image, the illumination light in a wavelength range in which an absorption coefficient of hemoglobin in blood is high is used to display an image with the blood vessels of a specific depth emphasized on the monitor. To observe the oxygen saturation image, an oxygen saturation level is calculated using the illumination light in a wavelength range in which absorbance varies depending on an amount of the hemoglobin in blood. The oxygen saturation level is imaged and displayed on the monitor.

The observation of the oxygen saturation level is considered to be effective in finding the cancer because cancer tissue is in a hypoxic or low-oxygen state. For example, in U.S. patent application Publication No. 2011/0237884 (corresponding to Japanese Patent Laid-Open Publication No. 2011-194151), three types of narrowband light (with the peak wavelengths of 405 nm, 440 nm, and 560 nm, respectively) in a blue band or three types of narrowband light (with the peak wavelengths of 540 nm, 560 nm, and 580 nm, respectively) in a green band are used. The image sensor images the region of interest while the three types of narrowband light are emitted sequentially toward the region of interest on a frame-by-frame basis. Thus, three frames of image data are acquired.

There are time lags between the acquisitions of the three frames of image data, resulting in positional shifts among the images of the three respective frames. To solve the problem, a means for extracting blood vessels is used to extract corresponding blood vessels in the respective images, and shift amounts of the images are calculated to align the corresponding blood vessels with each other. One of images of the three frames is moved by the shift amount relative to the image of the reference frame, and the remaining image is also moved by the shift amount relative to the image of the reference frame. Thus, the images of the three frames are aligned with each other. Thereafter, an oxygen saturation level of the blood vessel is calculated on a pixel-by-pixel basis from the image data of the three frames. Then, an oxygen saturation image representing distribution of the oxygen saturation levels is produced and displayed in pseudo-color on the monitor.

Absorption characteristics of hemoglobin and scattering characteristics of digestive tract mucosa significantly vary depending on a wavelength band. Hence, shapes of the blood vessels observed with the three respective types of wavelengths are different from each other. In the U.S. patent application Publication No. 2011/0237884, it is difficult to perform accurate registration or alignment of images because the shift amount between the images of different wavelengths is calculated.

The blood vessels are classified into surface blood vessels and subsurface (medium-depth and deep) blood vessels according to their depth from the surface. It is necessary to calculate the oxygen saturation levels of the blood vessels including both the surface and subsurface blood vessels. To detect the surface blood vessels, the narrowband light in a blue wavelength range is effective. To detect the medium-depth blood vessels, the narrowband light in a green wavelength range is effective. To detect the deep blood vessels, the narrowband light in a red wavelength range is effective. Accordingly, a blue image, a green image, and a red image are necessary to calculate the oxygen saturation levels of the surface and subsurface blood vessels. In the blue image, the surface blood vessels are emphasized while the subsurface blood vessels are inconspicuous. In the red image, on the contrary, the subsurface blood vessels are emphasized while the surface blood vessels are inconspicuous. To register or align the images of the respective frames with each other, the shift amount is calculated from the positions of the corresponding blood vessels in the blue and red images, for example. In this case, the image with the surface blood vessels emphasized is compared with the image with the inconspicuous surface blood vessels. As a result, the shift amount cannot be calculated accurately, making the registration difficult.

SUMMARY OF INVENTION

An object of the present invention is to provide an endoscope system, a processor device thereof, and an image producing method capable of precisely aligning images between frames.

In order to achieve the above objects, an endoscope system of the present invention comprises a lighting section, an image signal acquisition section, a shift amount calculator, a registration section, an oxygen saturation image generator, and a display section. The lighting section applies at least first illumination light and second illumination light, in respective frames, to a region of interest. A wavelength range of the first illumination light is different from a wavelength range of the second illumination light. The region of interest includes a blood vessel. The image signal acquisition section has a color image sensor with an array of pixels of at least three primary colors. The image signal acquisition section images the region of interest in the each frame. The image signal acquisition section images the region of interest illuminated with the first illumination light to acquire three color signals of a first frame. The image signal acquisition section images the region of interest illuminated with the second illumination light to acquire three color signals of a second frame. The shift amount calculator calculates a shift amount between an image of the first frame and an image of the second frame based on the color signals of same color. The registration section aligns images of predetermined color signals, used for calculating an oxygen saturation level of hemoglobin in blood, out of the color signals of the first and second frames based on the shift amount. The oxygen saturation image generator produces an oxygen saturation image of the oxygen saturation level based on the predetermined color signals aligned. The display section displays the oxygen saturation image.

It is preferable that the three color signals are a blue signal, a green signal and a red signal, and each of the first and second illumination light is white light, and the shift amount calculator calculates the shift amount between the green images produced based on the green signals.

It is preferable that the blue signal of the first frame, and the green and red signals of the second frame are used for calculating the oxygen saturation level, and the registration section moves the blue signal of the first frame to be aligned with the green and red signals of the second frame.

It is preferable that the first and second illumination light is produced by wavelength conversion of respective narrowband light, having different wavelength ranges, with a wavelength converter. It is preferable that the each narrowband light is laser beams. It is preferable that the center wavelengths of the laser beams are 473 nm and 445 nm, respectively.

It is preferable that the lighting section applies the first illumination light, the second illumination light, and third illumination light, in respective frames, to the region of interest. A wavelength range of the third illumination light is different from the wavelength range of each of the first and second illumination light. The image signal acquisition section images the region of interest in the each frame. It is preferable that the image signal acquisition section images the region of interest illuminated with the first illumination light to acquire the three color signals of the first frame. It is preferable that the image signal acquisition section images the region of interest illuminated with the second illumination light to acquire the three color signals of the second frame. It is preferable that the image signal acquisition section images the region of interest illuminated with the third illumination light to acquire three color signals of a third frame. It is preferable that the shift amount calculator calculates a first shift amount between images of the color signals of same color of the first and second frames and a second shift amount between images of the color signals of same color of the second and third frames. It is preferable that the registration section aligns images of predetermined color signals, used for calculating the oxygen saturation level, out of the color signals of the first, second, and third frames based on the first and second shift amounts.

A processor device for an endoscope system of the present invention comprises a receiver, a shift amount calculator, a registration section, and an oxygen saturation image generator. The receiver receives the three color signals of each of the first and second frames from the endoscope device. The shift amount calculator calculates a shift amount between an image of the first frame and an image of the second frame based on the color signals of same color. The registration section aligns images of predetermined color signals, used for calculating an oxygen saturation level of hemoglobin in blood, out of the color signals of the first and second frames based on the shift amount. The oxygen saturation image generator produces an oxygen saturation image of the oxygen saturation level based on the predetermined color signals aligned.

An image producing method of the present invention comprises an acquiring step, a calculating step, a registering step, and a producing step. In the acquiring step, at least first illumination light and second illumination light having different wavelength ranges is applied, in respective frames, to a region of interest including a blood vessel. The region of interest is imaged in the each frame with a color image sensor having an array of pixels of at least three primary colors. The color image sensor images the region of interest illuminated with the first illumination light to acquire three color signals of a first frame. The color image sensor images the region of interest illuminated with the second illumination light to acquire three color signals of a second frame. In the calculating step, a shift amount between an image of the first frame and an image of the second frame is calculated based on the color signals of same color. In the aligning step, images of predetermined color signals, used for calculating an oxygen saturation level of hemoglobin in blood, out of the color signals of the first and second frames are aligned based on the shift amount. In the producing step, an oxygen saturation image of the oxygen saturation level is produced based on the predetermined color signals aligned.

According to the present invention, the shift amount between the images, produced based on the color signals of the same color, of the respective frames is calculated to align the frames with each other. Thereby, the color signals are precisely aligned with each other. An oxygen saturation level is imaged based on the precisely aligned color signals. Thereby, information of the oxygen saturation level is displayed accurately. Surface and subsurface blood vessels in the images are precisely aligned with each other.

BRIEF DESCRIPTION OF DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 18 is an explanatory view illustrating calculation of a shift amount between frames and a registration process of another embodiment;

DESCRIPTION OF THE PREFERRED EMBODIMENTS

Figure 1:
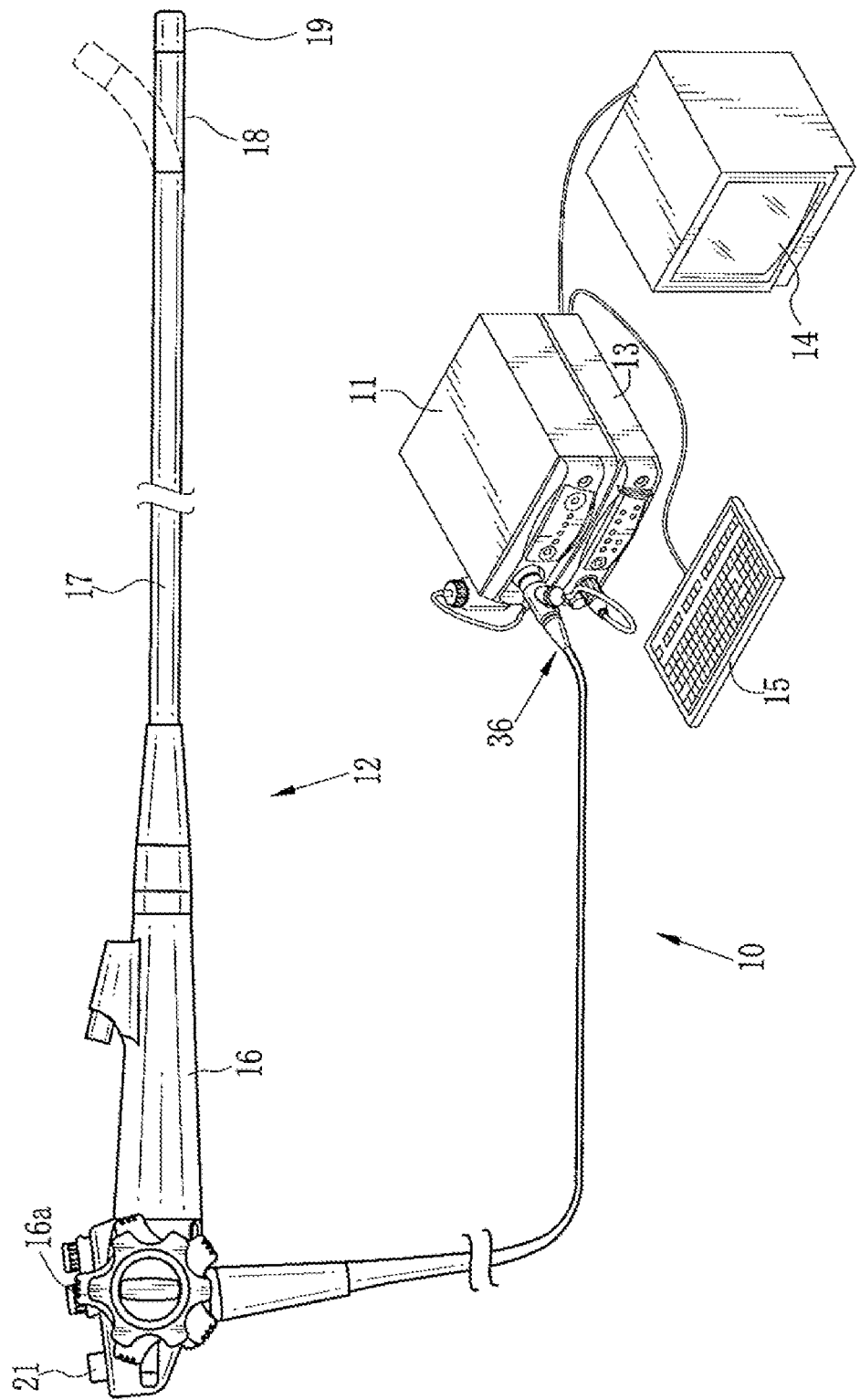
FIG. 1 is an external view of an endoscope system.

As shown in FIG. 1, an endoscope system 10 is provided with a light source device 11, an endoscope device 12, a processor device 13, a display device 14, and an input device 15. The light source device 11 generates illumination light. The endoscope device 12 images a region of interest in a subject while irradiating the region of interest with the illumination light. The processor device 13 performs image processing of the image signal acquired by imaging with the endoscope device 12. The display device 14 displays an endoscopic image, produced by the image processing, and the like. The input device 15 is composed of a keyboard and the like.

The endoscope device 12 is provided with a flexible tube portion 17, a bending portion 18, and a distal portion 19 in this order from a handling section 16 side. The flexible tube portion 17 is bent in and along a body cavity. Two angle knobs 16$a$ are disposed on the handling section 16. The bending portion 18 is bent in two directions orthogonal to each other by rotating the two angle knobs 16$a$. With the combination of the bending in two directions, the bending portion 18 is bent at any desired angle and in any desired direction to direct the distal portion 19 toward a region of interest.

The endoscope system 10 is provided with a normal mode and an oxygen saturation mode. In the normal mode, a normal image is displayed on the display device 14. The normal image is a subject image of visible light in a wavelength range from blue to red. In the oxygen saturation mode, an oxygen saturation image is displayed on the display device 14. The oxygen saturation image is an image representing an oxygen saturation level of hemoglobin in blood in a region of interest. These modes are switched as necessary based on information inputted with a changeover switch 21 of the endoscope device 12, the input device 15, or the like.

Figure 2:
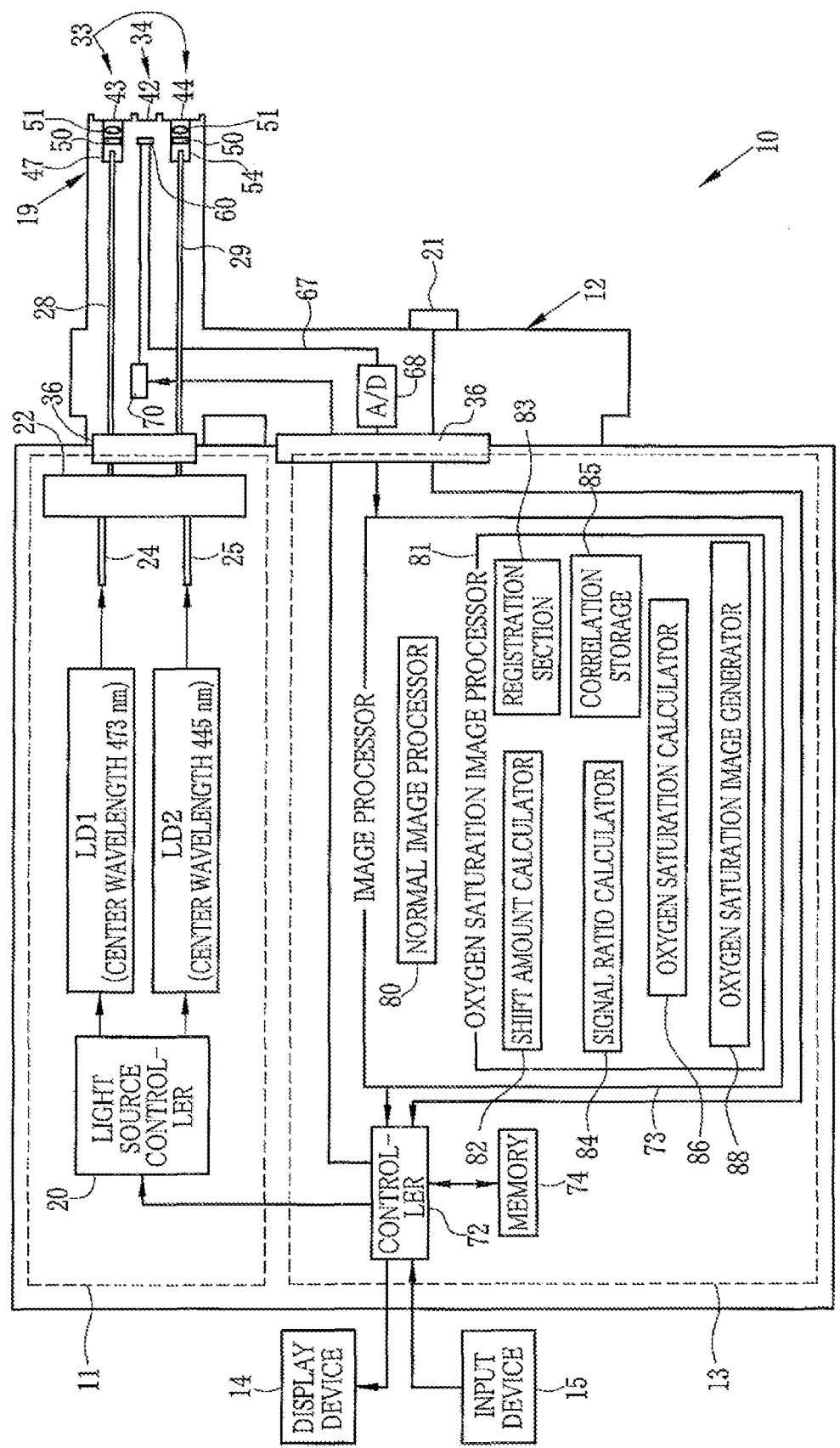
FIG. 2 is a block diagram of the endoscope system.

As shown in FIG. 2, the light source device 11 is provided with two types of lasers LD1 and LD2, and a light source controller 20. The laser LD1 emits first laser beams with the center wavelength of 473 nm. The first laser beams are subjected to wavelength conversion through a phosphor 50 disposed in the distal portion 19 of the endoscope device 12. The phosphor 50 converts the first laser beams into first white light (pseudo-white light). The laser LD2 emits second laser beams with the center wavelength of 445 nm. The second laser beams are also subjected to the wavelength conversion through the phosphor 50 and converted into second white light. Note that the first laser beams are preferably in the wavelength range of 460 to 480 nm. The second laser beams are preferably in the wavelength range of 440 to 460 nm.

The first laser beams emitted from the laser LD1 are incident on an optical fiber 24 through a condenser lens (not shown). The second laser beams emitted from the laser LD2 are incident on an optical fiber 25 through a condenser lens (not shown). Note that the lasers LD1 and LD2 may be broad area type InGaN laser diodes, InGaNAs laser diodes, or GaNAs laser diodes, for example.

The light source controller 20 controls or adjusts emission timing of each of the lasers LD1 and LD2. In this embodiment, in the normal mode, the laser LD2 is turned on while the laser LD1 is turned off. In the oxygen saturation mode, the lasers LD1 and LD2 are switched to each other on a frame-by-frame basis. Namely, for example, the laser LD1 is turned on while the laser LD2 is turned off in one frame. In the next frame, the LD1 is turned off while the laser LD2 is turned on.

A splitter 22 splits the first laser beams from the optical fiber 24 into two paths. The two paths of laser beams are incident on respective light guides 28 and 29. The splitter 22 also splits the second laser beams from the optical fiber 25 into two paths. The two paths of laser beams are incident on the respective light guides 28 and 29. Each of the light guides 28 and 29 is composed of a fiber bundle of optical fibers.

The endoscope device 12 is an electronic endoscope. The endoscope device 12 is provided with a lighting section 33, an imaging section 34, and a connector 36. The lighting section 33 applies the two paths of laser beams, transmitted through the light guides 28 and 29, to the region of interest. The imaging section 34 images the region of interest. The connector 36 connects the endoscope device 12, the light source device 11, and the processor device 13 in a detachable manner.

The lighting section 33 is provided with two lighting windows 43 and 44. The imaging section 34 is provided between the lighting windows 43 and 44. Each of the lighting windows 43 and 44 applies the first or second white light to the region of interest. The imaging section 34 is provided with a capture window 42 located at the approximate center of the distal portion 19. The capture window 42 receives reflection light reflected from the region of interest.

Projection units 47 and 54 are accommodated behind the lighting windows 43 and 44, respectively. The first or second laser beams from the light guide 28 are projected from the projection unit 47 to the phosphor 50. The first or second laser beams from the light guide 29 are projected from the projection unit 54 to another phosphor 50. Upon irradiation with the first laser beams, the phosphors 50 emit the first white light toward the region of interest through respective lenses 51. Upon irradiation with the second laser beams, the phosphors 50 emit the second white light toward the region of interest through the respective lenses 51.

The phosphor 50 includes fluorescent substances, for example, YAG or BAM(BaMgAl$_{10}$O$_{17}$). These fluorescent substances absorb apart of the first and second laser beams from the lasers LD1 and LD2. When irradiated with the first or second laser beams, the excited phosphor 50 emits light (fluorescence) from green to red. The fluorescence and the excitation light (the first or second laser beams) unabsorbed by and transmitted through the phosphor 50 is combined to produce the white light (pseudo-white light).

Note that the phosphor 50 preferably has a substantially rectangular parallelepiped shape. The fluorescent substances may be formed into the substantially rectangular parallelepiped phosphor 50 with binder. A mixture of the fluorescent substances may be formed into the substantially rectangular parallelepiped phosphor 50 on resin such as inorganic glass. The product sold under the trademark MICRO WHITE® (or MW, registered trade mark) may be used as the phosphor 50.

Figure 3:
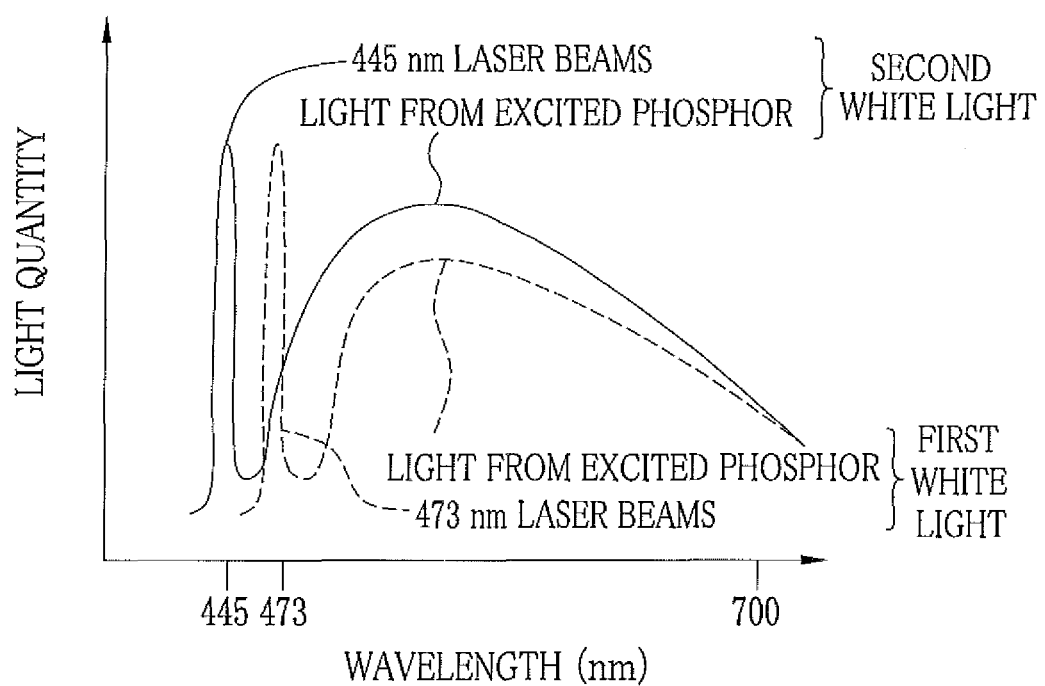
FIG. 3 is a graph illustrating emission spectra of first and second white light.

As shown in FIG. 3, when the first laser beams are incident on the projection units 47 and 54, the first white light having the wavelength range of the first laser beams with the center wavelength of 473 nm, and the wavelength range of approximately 480 nm to 700 nm is emitted toward the region of interest. The emission intensity of the fluorescence excited by the first laser beams increases in the wavelength range of approximately 480 nm to 700 nm. When the second laser beams are incident on the projection units 47 and 54, the second white light having the wavelength range of the second laser beams with the center wavelength of 445 nm, and the wavelength range of approximately 460 nm to 700 nm is emitted toward the region of interest. The emission intensity of the fluorescence excited by the second laser beams increases in the wavelength range of approximately 460 nm to 700 nm.

Note that the white light in the present invention does not necessarily include all of the wavelength components of visible light. The above-described pseudo white light is used by way of example. The white light may include the light in a specific wavelength range such as the light of a primary color, red (R), green (G), or blue (B). The white light of the present invention may be the light having wavelength components from green to red or the light having wavelength components from blue to green, for example.

An optical system such as an objective lens unit (not shown) is provided behind the capture window 42. The objective lens unit captures image light of the region of interest in the subject. An image sensor 60 is provided behind the objective lens unit. The image sensor 60 receives the image light of the region of interest to image it. The image sensor 60 is a CCD (Charge Coupled Device) or a CMOS (Complementary Metal-Oxide Semiconductor), for example.

Figure 4A:
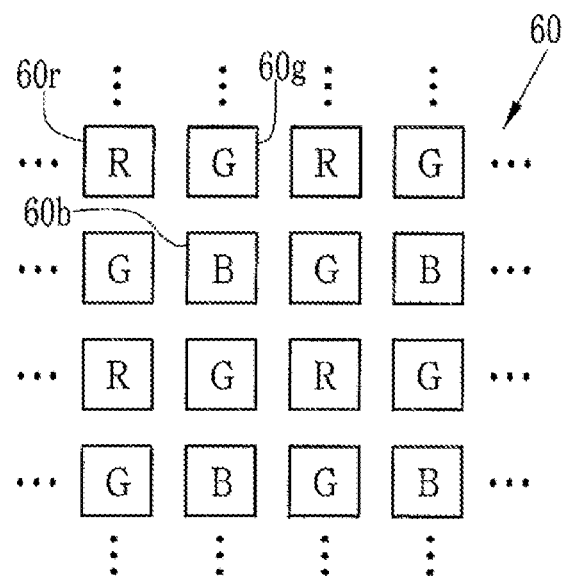
FIG. 4A illustrates an arrangement of B, G, and R pixels of the image sensor.
Figure 4B:
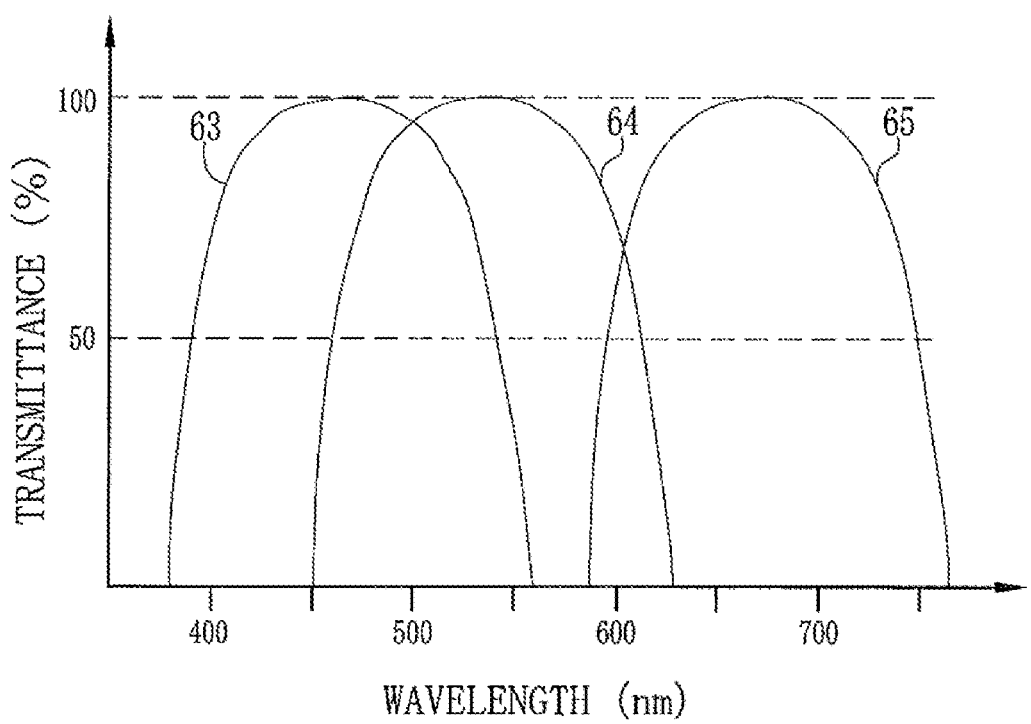
FIG. 4B is a graph illustrating spectral transmittance of each of the B, G, and R pixels.

The image sensor 60 is controlled by an imaging controller 70. A light receiving surface (imaging surface) of the image sensor 60 receives the light from the objective lens unit. The image sensor 60 photoelectrically converts the received light into an image signal (analog signal) and outputs the image signal. The image sensor 60 is a color CCD. As shown in FIG. 4A, a pixel group is arranged in a matrix array in the light receiving surface of the image sensor 60. The pixel group is composed of a plurality of pixel sets, each including a B pixel 60$b$, a. G pixel 60$g$, and an R pixel 60$r$. The B pixel 60$b$ is provided with a B color filter. The G pixel 60$g$ is provided with a G color filter. The R pixel 60$r$ is provided with an R color filter. The B, G, and R color filters exhibit spectral transmittance in blue, green, and red bands as shown by curves 63, 64, and 65, respectively, in FIG. 4B. Accordingly, the reflection light from the region of interest illuminated with the first or second white light passes through R, G, and B color filters in accordance with the wavelength of the reflection light.

The analog image signal outputted from the image sensor 60 is inputted to an A/D converter 68 through a scope cable 67. The A/D converter 68 converts the analog image signal into a digital image signal in accordance with a voltage level of the analog image signal. The digital image signal is inputted to an image processor 73 of the processor device 13 through the connector 36.

The processor device 13 is provided with a controller 72, the image processor 73, and a memory 74. The display device 14 and the input device 15 are connected to the controller 72.

The controller 72 controls operation of each of the image processor 73, the light source controller 20 of the light source device 11, the imaging controller 70 of the endoscope device 12, and the display device 14 based on information inputted from the input device 15 or the changeover switch 21 of the endoscope device 12.

The image processor 73 is provided with a normal image processor 80 and an oxygen saturation image processor 81. The image processor 73 performs image processing of the image signal acquired from the endoscope device 12. The normal image processor 80 performs image processing of the image signal acquired in the normal mode. Thus, the normal image is produced.

Figure 5A:
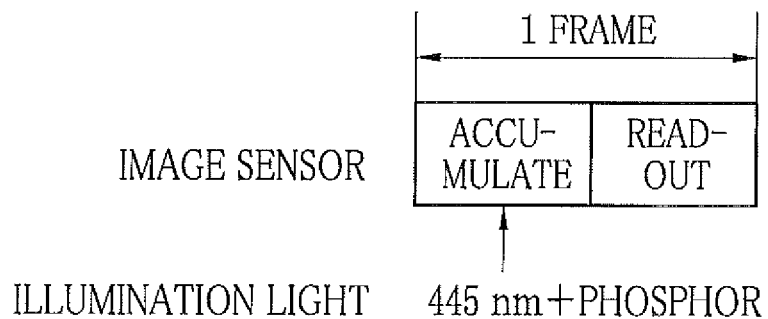
FIG. 5A is an explanatory view describing imaging control of an image sensor in a normal mode.

As shown in FIG. 5A, in the normal mode, two steps, an accumulation step and a reading step are performed in one frame period. In the accumulation step, charge generated by the photoelectric conversion of the second white light (denoted as "445 nm+phosphor", meaning that the second white light is produced by applying the second laser beams of 445 nm to the phosphor 50) is accumulated. In the reading step, the charge accumulated is read out. The accumulation step and reading steps are repeated alternately in the normal mode.

Figure 5B:
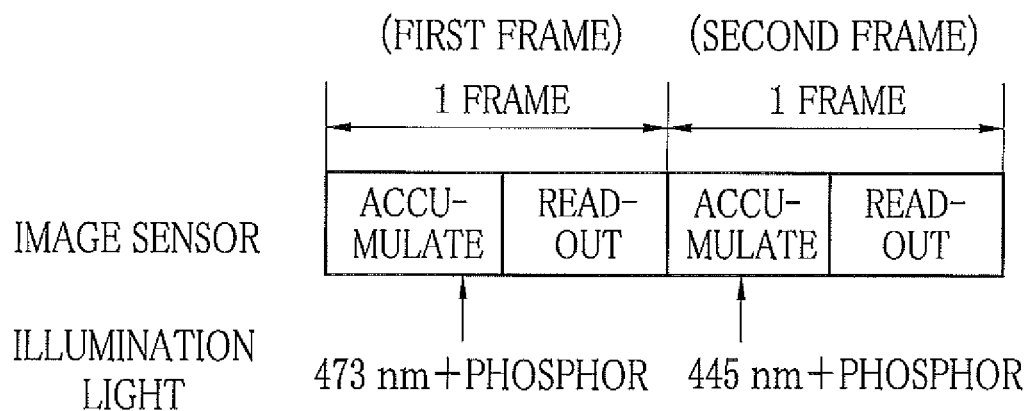
FIG. 5B is an explanatory view describing imaging control of the image sensor in an oxygen saturation mode.

In the oxygen saturation mode, as shown in FIG. 5B, two steps, an accumulation step and a reading step are performed in each of first and second frames. In the accumulation step of the first frame, charge generated by the photoelectric conversion of the first white light (denoted as "473 nm+MW", meaning that the first white light is produced by applying the first laser beams of 473 nm to the phosphor 50) is accumulated. In the reading step of the first frame, the charge accumulated is read out. In the accumulation step of the second frame, the charge generated by the photoelectric conversion of the second white light is accumulated. In the reading step of the second frame, the charge accumulated is read out. The imaging control on the two frames is repeated in the oxygen saturation mode.

In the first frame in the oxygen saturation mode, a blue signal B1, a green signal G1, and a red signal R1 are outputted from the respective B, G, and R pixels of the image sensor 60. In the second frame in the oxygen saturation mode, a blue signal B2, a green signal G2, and a red signal R2 are outputted from the B, G, and R pixels, respectively.

Figure 6:
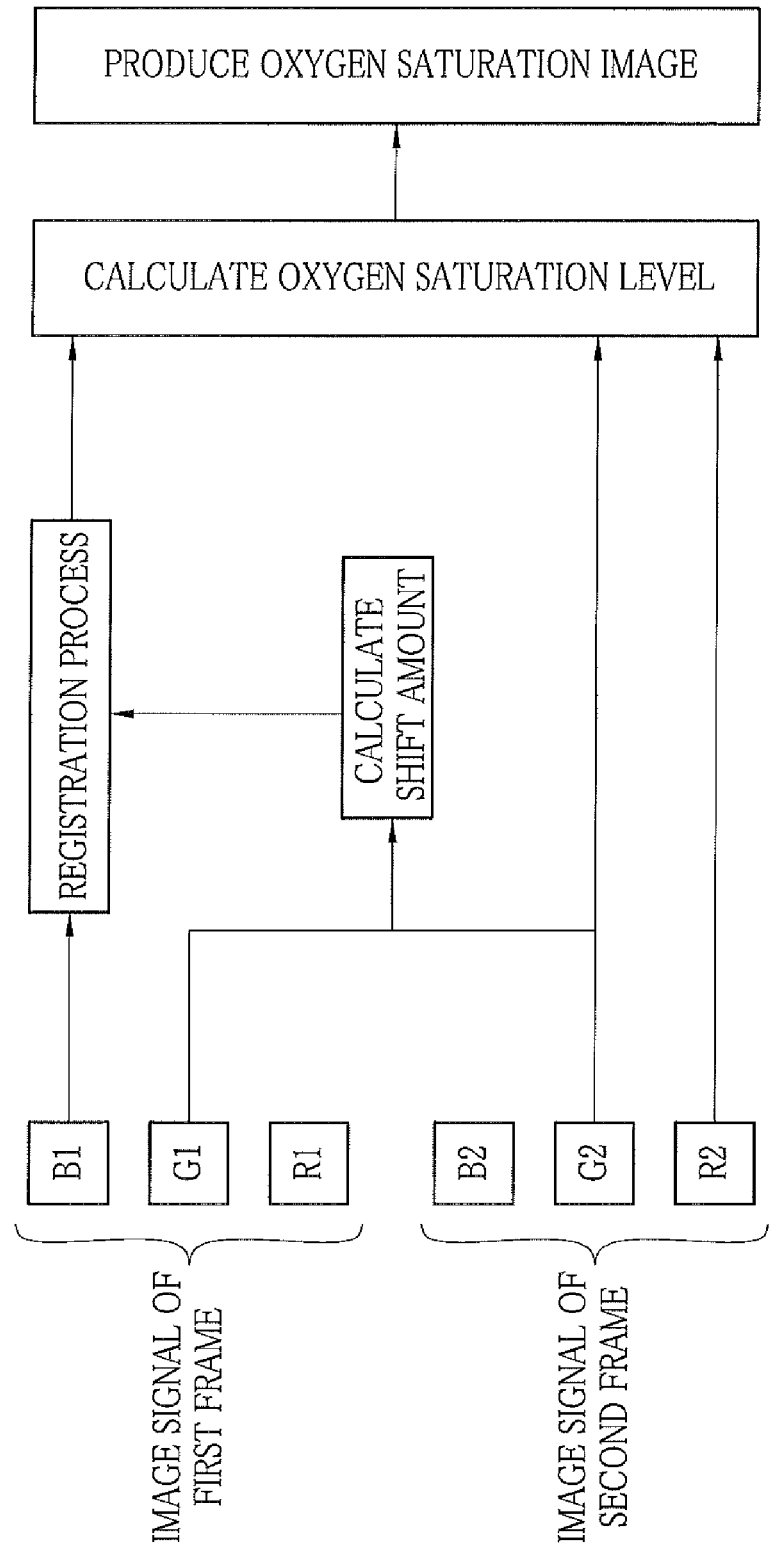
FIG. 6 is an explanatory view describing calculation of a shift amount between frames and a registration process.

As shown in FIG. 6, based on the image signal inputted from the endoscope device 12, the oxygen saturation image processor 81 calculates an oxygen saturation level of hemoglobin in blood in the region of interest and produces an oxygen saturation image representing the oxygen saturation level. To calculate the oxygen saturation level, as shown in FIG. 6, the blue signal B1 of the first frame and the green signal G2 and the red signal R2 of the second frame are used by way of example.

Before the calculation of oxygen saturation level, a registration or alignment process is performed to correct alignment error (color registration error and image registration error between first and second frames) among the signals B1, G2, and R2 used for the calculation of oxygen saturation level. A shift amount between the frames is calculated using the images of the same color. Generally, blood vessels are imaged differently in accordance with the wavelength used, due to absorption characteristics of hemoglobin and scattering characteristics of digestive tract mucosa. For this reason, the shift amount (or the shift amount between the images) calculated using the image signals of the same color is more accurate than that calculated using the image signals of different colors (for example, the blue signal and the red signal).

In this embodiment, the shift amount between the images of the respective frames is calculated using the green signals G1 and G2.

Figure 7:
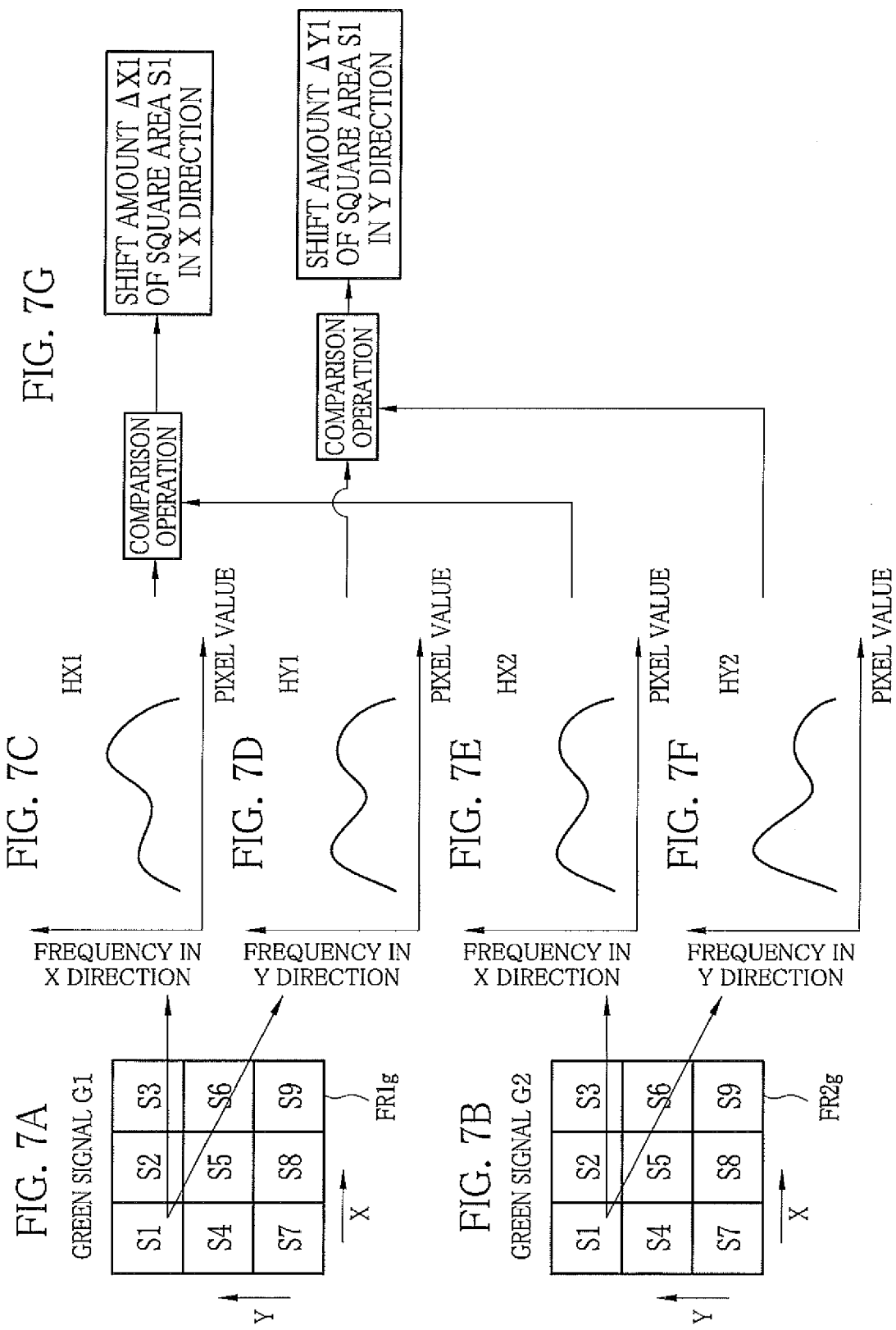
FIGS. 7A to 7G are explanatory views describing a method for calculating a shift amount $\Delta X1$ of a square area S1 in X direction and a shift amount $\Delta Y1$ of the square area S1 in Y direction.

The oxygen saturation image processor 81 is provided with a shift amount calculator 82, a registration section 83, a signal ratio calculator 84, correlation storage 85, an oxygen saturation calculator 86, and an oxygen saturation image generator 88. The shift amount calculator 82 calculates a shift amount $\Delta F$ between the image signal of the first frame and the image signal of the second frame (more precisely, a shift amount $\Delta F$ between the images of the respective frames). The shift amount $\Delta F$ is calculated using the green signal G1 of the first frame and the green signal G2 of the second frame. The signal characteristics of the green signal G1 are similar to those of the green signal G2. First, as shown in FIGS. 7A and 7B, all the pixels of each of the green signals G1 and G2 of one frame are segmented into nine square areas S1 to S9 arranged 3×3 in longitudinal and lateral directions. Here, X direction refers to the longitudinal direction of the image signal, for example, the green signals G1 and G2. Y direction refers to the lateral direction of the image signal.

Next, as shown in FIGS. 7C to 7F, a cumulative histogram HX1 of the square area S1 of the green signal G1 in the X direction is created, and a cumulative histogram HY1 of the square area S1 of the green signal G1 in the Y direction is created. Each of the cumulative histograms represents frequency (the number of occurrences) of pixel values in the square area S1 in the X or Y direction. In the cumulative histogram, the vertical axis represents the frequency, and the horizontal axis represents the pixel value. In a similar manner, a cumulative histogram HX2 of the square area S1 of the green signal G2 in the X direction is created, and a cumulative histogram HY2 of the square area S1 of the green signal G2 in the Y direction is created.

Then, as shown in FIG. 7G, a shift amount $\Delta X1$ of the square area S1 in the X direction is calculated from comparison operation between the cumulative histogram HX1 and the cumulative histogram HX2. When the pattern of the cumulative histogram HX1 is substantially the same as that of the cumulative histogram HX2, the shift amount $\Delta X1$ is "0" or extremely small. The shift amount $\Delta X1$ increases as the difference between the patterns of the cumulative histograms HX1 and HX2 increases. In a similar manner, a shift amount $\Delta Y1$ of the square area S1 in the Y direction is calculated from the comparison operation between the cumulative histograms HY1 and HY2.

When the shift amounts $\Delta X1$ and $\Delta Y1$ of the square area S1 are calculated, shift amounts $\Delta X2$ to $\Delta X9$ and shift amounts $\Delta Y2$ to $\Delta Y9$ of the square areas S2 to S9 are calculated, respectively, in a manner similar to the above. After the shift amounts $\Delta X1$ to $\Delta X9$ and the shift amounts $\Delta Y1$ to $\Delta Y9$ of all the square areas S1 to S9 between the green signals G1 and G2 are calculated, a total shift amount (hereinafter simply referred to as the shift amount) $\Delta Fx$ of the whole signal in the X direction and a total shift amount (hereinafter simply referred to as the shift amount) $\Delta Fy$ of the whole signal in the Y direction are calculated as shown by the expressions (1) and (2).

$$\Delta Fx = \Delta X1 + \Delta X2 + \ldots + \Delta X9 \quad (1)$$

$$\Delta Fy = \Delta Y1 + \Delta Y2 + \ldots + \Delta Y9 \quad (2)$$

Figure 8:
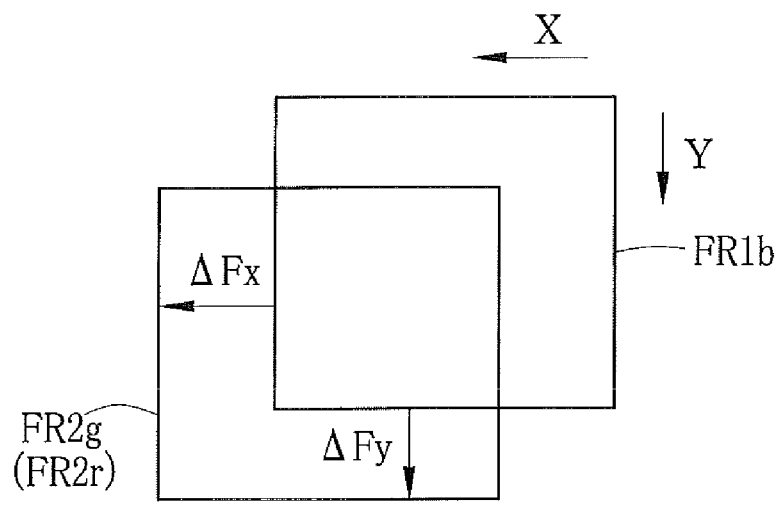
FIG. 8 is an explanatory view illustrating registration of a blue image FR1$b$ and a green image FR2$g$.

As shown in FIG. 8, the shift amounts $\Delta Fx$ and $\Delta Fy$ correspond to the shift amount between the images of the first and second frames. FIG. 8 illustrates the shift between the images conceptually. The shift amount calculator 82 calculates the shift amounts $\Delta Fx$ and $\Delta Fy$.

The registration section 83 aligns the blue signal B1 of the first frame, the green signal G2 of the second frame, and the red signal R2 of the second frame using the shift amounts $\Delta Fx$ and $\Delta Fy$ between the images. The blue signal B1, the green signal G2, and the red signal R2 are used for the calculation of oxygen saturation level. The registration section 83 moves a blue image FR1$b$, composed of the blue signal B1 of the first frame, by the shift amounts $\Delta Fx$ and $\Delta Fy$ in a direction to cancel out the shift between the images of the respective first and second frames. This cancels out the shift between the images of the respective frames. Thus, the pixels in the respective blue image FR1$b$ of the first frame, green image FR2$g$ and red image FR2$r$ of the second frame are aligned with each other. The green image FR2$g$ is composed of the green signal G2 of the second frame. The red image FR2$r$ is composed of the red signal R2 of the second frame. Note that, conversely, the images FR2$g$ and FR2$r$ of the second frame may be moved to be aligned with the blue image FR1$b$ of the first frame. The registration (alignment) allows the accurate calculation of oxygen saturation level.

After the registration, the signal ratio calculator 84 calculates signal ratios B1/G2 and R2/G2. The signal ratio B1/G2 is a signal ratio between the corresponding pixels in the blue image FR1$b$ of the first frame and the green image FR2$g$ of the second frame. The signal ratio R2/G2 is a signal ratio between the corresponding pixels in the red image FR2$r$ of the second frame and the green image FR2$g$ of the second frame. The signal ratios are calculated for every pixel in the first and second frames. Note that the signal ratio may be calculated only for the pixels in a vascular portion of the image signal. The vascular portion is identified based on a difference between an image signal of the vascular portion and an image signal of a portion other than the vascular portion.

Figure 9:
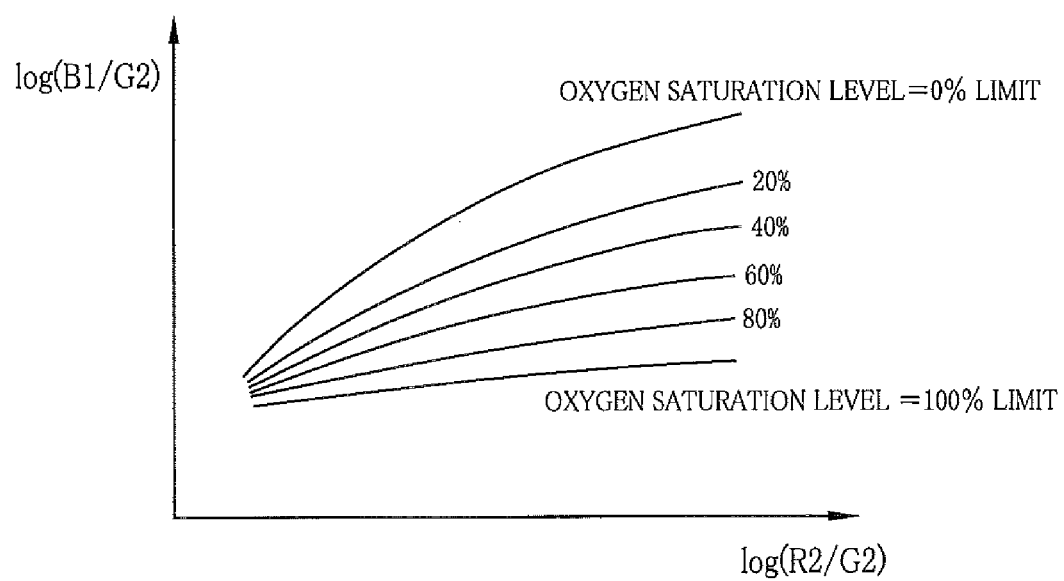
FIG. 9 is a graph illustrating correlation among oxygen saturation level and signal ratios B1/G2 and R2/G2.

The correlation storage 85 stores the correlation among the signal ratios B1/G2, R2/G2 and the oxygen saturation level. As shown in FIG. 9, the correlation is stored in a two-dimensional table in which contour lines of the oxygen saturation level are defined in a two dimensional space. The positions and shapes of the contour lines are obtained from physical simulation of light scattering, and vary according to the blood volume. For example, a space between the contour lines increases or decreases with a change in blood volume. Here, the signal ratios B1/G2 and R2/G2 are stored in log scale.

Figure 10:
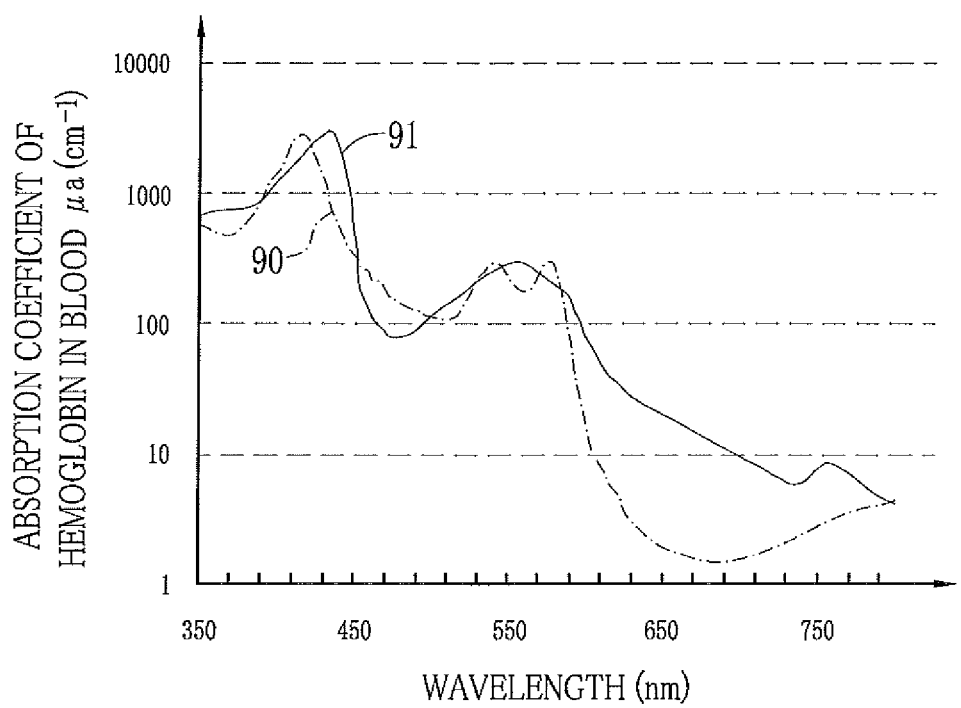
FIG. 10 is a graph illustrating absorption coefficient of hemoglobin.

The above-described correlation is closely related to light absorption properties and light scattering properties of oxyhemoglobin and deoxyhemoglobin shown in FIG. 10. Here, a curve 90 shows an absorption coefficient of oxyhemoglobin. A curve 91 shows an absorption coefficient of deoxyhemoglobin. It is easy to obtain information on the oxygen saturation level with the light at 473 nm, for example, where a difference between the absorption coefficient of the oxyhemoglobin and the absorption coefficient of the deoxyhemoglobin is large. However, the blue signal B1 including a signal component corresponding to the light at 473 nm is highly dependent on both the oxygen saturation level and the blood volume. To calculate the oxygen saturation level accurately without depending on the blood volume, the signal ratios B1/G2 and R2/G2 are used in addition to the blue signal B1. The signal ratios B1/G2 and R2/G2 are calculated using the blue signal B1, the red signal R2, and the green signal G2. The red signal R2 corresponds to the light which varies depending mainly on the blood volume. The green signal G2 is a reference signal for the blue signal B1 and the red signal R2.

Figure 11:
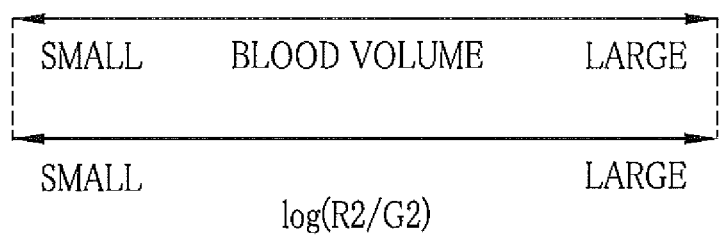
FIG. 11 is a graph illustrating correlation between blood volume and the signal ratio R2/G2.

Note that the correlation storage 85 also stores the correlation between the signal ratio R1/G1 and the blood volume as shown in FIG. 11. The correlation is stored in a one-dimensional table in which the blood volume increases with the increase in the signal ratio R1/G1. The correlation between the signal ratio R1/G1 and the blood volume is used for calculating the blood volume.

Based on wavelength dependence characteristics of the absorption coefficient of hemoglobin in blood, there are three important points.

1. In a wavelength range close to 470 nm (for example, in a blue wavelength range with the center wavelength of 470 nm±10 nm), the absorption coefficient varies significantly in accordance with a change in the oxygen saturation level.

2. When averaged in a green wavelength range from 540 nm to 580 nm, the absorption coefficient is likely to be unaffected by the oxygen saturation level.

3. In a red wavelength range from 590 nm to 700 nm, the absorption coefficient appears to vary significantly in accordance with a change in the oxygen saturation level. Actually, however, the absorption coefficient is likely to be unaffected by the oxygen saturation level because the value of the absorption coefficient is extremely small.

As shown in FIG. 9, the signal value of the signal ratio B1/G2 increases as the signal ratio R2/G2 increases (namely, the contour line of the oxygen saturation level=0% limit extends toward the upper right direction). This is because the blood volume and the signal ratio R2/G2 correlate with each other in such a way that the blood volume increases as the signal ratio R2/G2 increases. Of the signal values of the signals B1, G2, and R2, the signal value of the green signal G2 decreases the most, followed by the signal value of the blue signal B1, when the blood volume increases. This is because the absorption coefficient of the wavelength component (540 to 580 nm) in the green signal G2 is higher than that of the wavelength component (around 470 nm) in the blue signal B1 (see FIG. 10). Accordingly, in the signal ratio B1/G2, a decrease in the signal value G2 (denominator) is greater than that in the signal value B1 (numerator) as the blood volume increases. Namely, the signal ratio B1/G2 increases as the blood volume increases.

Figure 12:
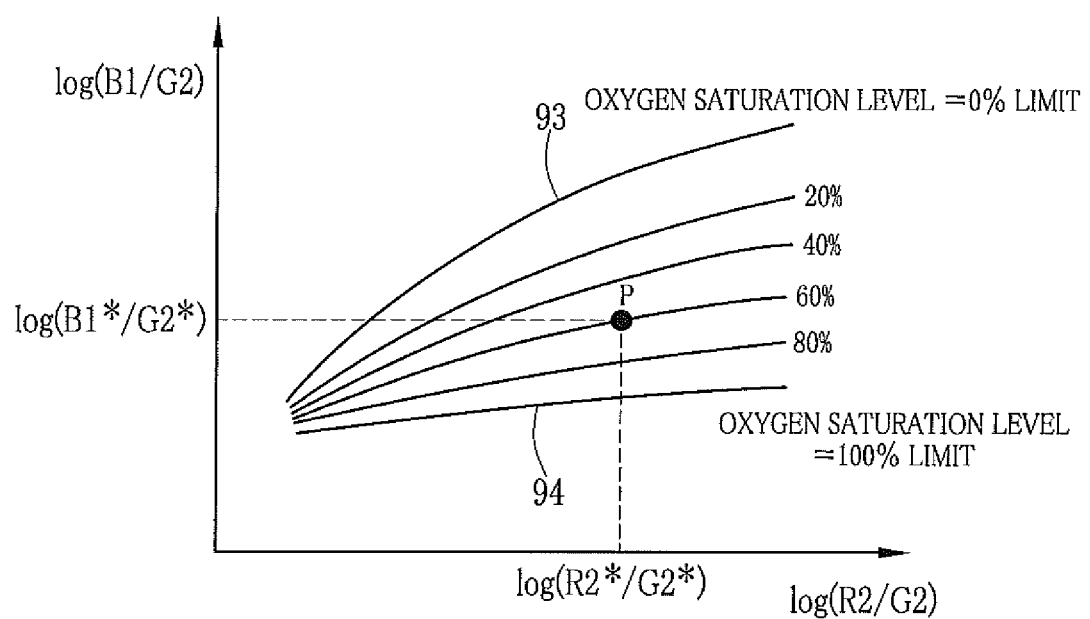
FIG. 12 is a graph describing how to obtain an oxygen saturation level from the signal ratio using the graph of FIG. 9.

The oxygen saturation calculator 86 calculates an oxygen saturation level in each pixel with the use of the correlation stored in the correlation storage 85 and the signal ratios B1/G2 and R2/G2 calculated by the signal ratio calculator 84. As shown in FIG. 12, a point P corresponding to the signal ratios B1*/G2* and R2*/G2*, calculated by the signal ratio calculator 84, is determined based on the correlation stored in the correlation storage 85. When the point P is located between a lower limit line 93 (oxygen saturation level=0% limit) and an upper limit line 94 (oxygen saturation level=100% limit), the oxygen saturation level is the percentage expressed by the contour line on which the point P is located. For example, in FIG. 12, the point P is located on the contour line of "60%", so that the percentage of the oxygen saturation level is 60%.

If the point P is located outside of the range between the lower limit line 93 and the upper limit line 94, for example, when the point P is located above the lower limit line 93, the oxygen saturation level is determined to be 0%. When the point P is located below the upper limit line 94, the oxygen saturation level is determined to be 100%. Note that when the point P is located outside of the range between the lower limit line 93 and the upper limit line 94, the reliability of the oxygen saturation level in the pixel may be reduced so as not to display the oxygen saturation level.

The oxygen saturation image generator 88 produces an oxygen saturation image based on the oxygen saturation level calculated by the oxygen saturation calculator 86. The oxygen saturation image is displayed on the display device 14.

The oxygen saturation image may be displayed in colors (referred to as "pseudo-colors" different from standard colors used in the normal image) corresponding to different oxygen saturation levels, for example. Alternatively, only a hypoxic or low oxygen region, in which the oxygen saturation level is less than a predetermined value, in the oxygen saturation image may be displayed in the pseudo-colors and a region other than that may be displayed in the standard colors used in the normal image.

Figure 13:
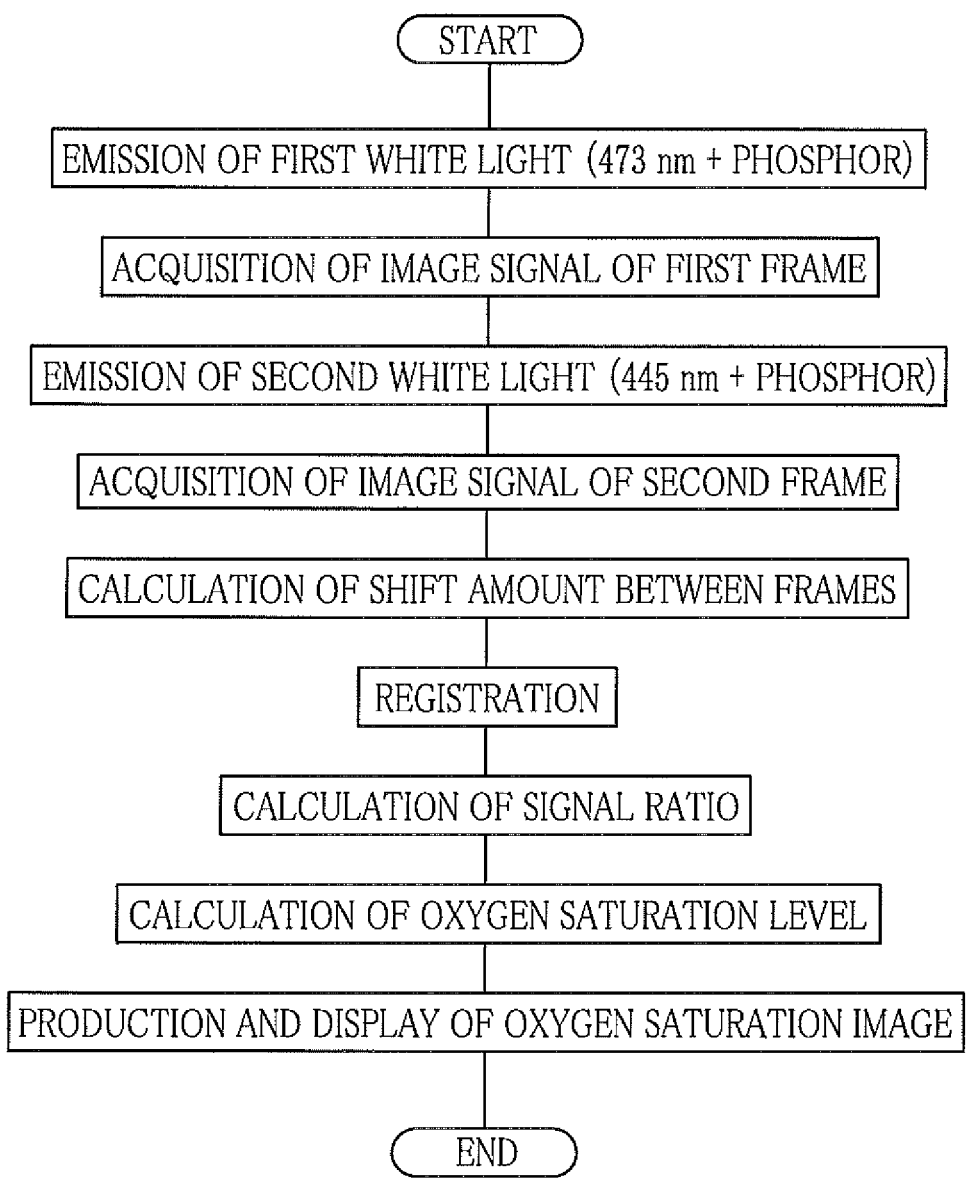
FIG. 13 is a flowchart illustrating a procedure in the oxygen saturation mode.

Next, referring to a flowchart in FIG. 13, operation of the present invention is described. When the normal mode is switched to the oxygen saturation mode using the changeover switch 21 of the endoscope device 12, the first laser beams with the center wavelength of 473 nm excite the phosphor 50 to emit the first white light. The first white light illuminates the region of interest. The image sensor 60, being the color CCD composed of the B, G, and R pixels, images the reflection light from the region of interest. Thereby, an image signal of the first frame is acquired. The image signal is composed of the blue signal B1, the green signal G1, and the red signal R1.

Thereafter, the second laser beams with the center wavelength of 445 nm excite the phosphor 50 to emit the second white light. The second white light illuminates the region of interest. The image sensor 60 images the reflection light from the region of interest. Thereby, an image signal of the second frame is acquired. The image signal is composed of the blue signal B2, the green signal G2, and the red signal R2.

When the image signal of the second frame is acquired, the shift amount calculator 82 calculates the shift amount ΔFx in the X direction and the shift amount ΔFy in the Y direction, between the green image FR1g of the first frame and the green image FR2g of the second frame. The shift amounts ΔFx and ΔFy are calculated based on the shift amount between the square areas S1, the shift amount between the square areas S2, the shift amount between the square areas S3, the shift amount between the square areas S4, the shift amount between the square areas S5, the shift amount between the square areas S6, the shift amount between the square areas S7, the shift amount between the square areas S8, and the shift amount between the square areas S9 of the green images FR1g and FR2g. Based on the shift amounts ΔFx and ΔFy, the blue image FR1b, the green image FR2g, and the red image FR2r, used for the calculation of oxygen saturation level, are aligned with each other.

Then, the signal ratio calculator 84 calculates the signal ratios B1/G2, and R2/G2 between the corresponding pixels in the images of the first and second frames or in the images of the second frame. The signal ratios B1/G2 and R2/G2 are calculated for every pixel. Thereafter, the oxygen saturation calculator 86 calculates the oxygen saturation level corresponding to the signal ratios B1/G2 and R2/G2, calculated by the signal ratio calculator 84, from the correlation stored in the correlation storage 85. The oxygen saturation level is calculated for every pixel. Based on the oxygen saturation levels, the oxygen saturation image is produced. The oxygen saturation image is displayed on the display device 14.

Figure 14:
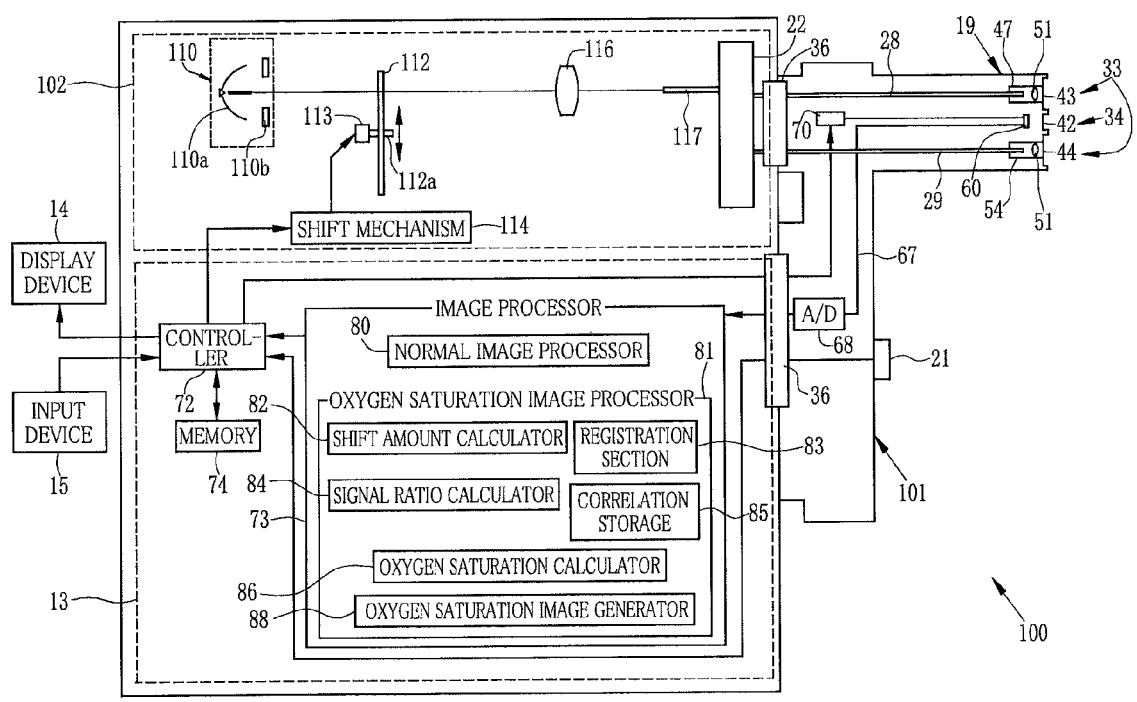
FIG. 14 is a block diagram of an endoscope system of another embodiment.

Note that, in the above embodiments, the illumination light from the semiconductor light source is used to illuminate the region of interest in the subject. Alternatively, a white light source such as a xenon lamp that emits broadband light may be used. In this case, a rotation filter is used to separate light of desired wavelength(s) from the broadband light to illuminate the region of interest (rotation filter method). In FIG. 14, an endoscope system 100 has a configuration similar to that of the endoscope system 10, except for an endoscope device 101 and a light source device 102. Hereinafter, the configuration of each of the endoscope device 101 and the light source device 102 and parts related to them are described. The descriptions of parts other than those are omitted.

The endoscope device 101 is different from the endoscope device 12 in that the lighting section 33 of the distal portion is not provided with the phosphor 50. The light from the light source device 102 is applied to the region of interest through the light guides 28 and 29. Other than that, the endoscope device 101 is similar to the endoscope device 12.

The light source device 102 is provided with a white light source 110, a rotation filter 112, a motor 113, and a shift mechanism 114. The white light source 110 emits broadband light BB (400 to 700 nm). The rotation filter 112 separates the broadband light BB into light of three colors, B, G, and R. The motor 113 is connected to a rotation axis 112a of the rotation filter 112 to rotate the rotation filter 112 at a constant rotation speed. The shift mechanism 114 shifts the rotation filter 112 in a radial direction.

The white light source 110 is provided with a light source body 110a and an aperture stop 110b. The light source body 110a emits the broadband light BB. The aperture stop 110b changes or adjusts a light quantity of the broadband light BB. The light source body 110a is composed of a xenon lamp, a halogen lamp, or a metal halide lamp, for example. The size of the opening of the aperture stop 110b is controlled by a light quantity controller (not shown).

Figure 15:
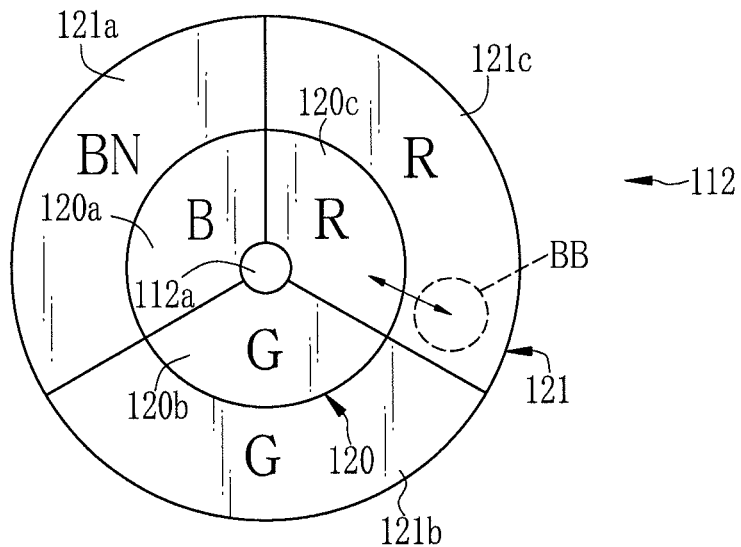
FIG. 15 illustrates a rotation filter.

As shown in FIG. 15, the rotation filter 112 is rotated about the rotation axis 112a connected to the motor 113. The rotation filter 112 is provided with a first filter area 120 and a second filter area 121 in this order in a radial direction from the rotation axis 112a. The first and second filter areas 120 and 121 have different blue pass-bands. One of the first and second filter areas 120 and 121 is set on the light path of the broadband light BB in accordance with the mode selected. In the normal mode, the first filter area 120 is set on the light path of the broadband light BB. In the oxygen saturation mode, the second filter area 121 is set on the light path of the broadband light BB. The shift mechanism 114 shifts the rotation filter 112 in the radial direction to switch from the first filter area 120 to the second filter area 121 and vice versa.

Figure 16:
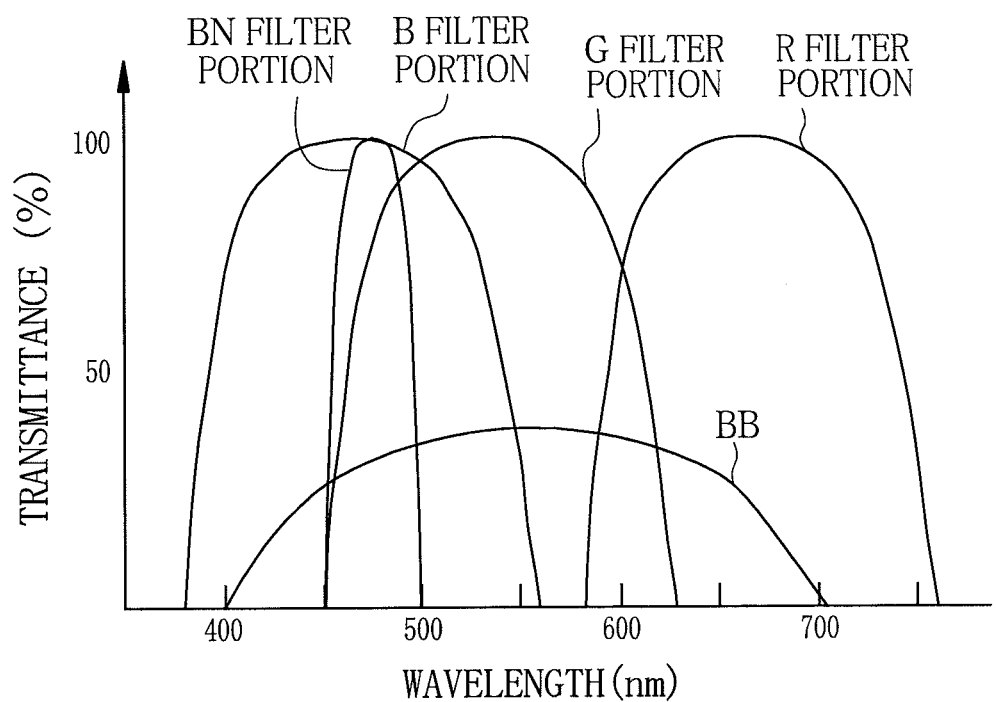
FIG. 16 is a graph illustrating spectral transmittance of each of a B filter portion, a G filter portion, an R filter portion, and a BN filter portion of the rotation filter.

The first filter area 120 is provided with a B filter portion 120a, a G filter portion 120b, and an R filter portion 120c, each in a shape of a sector with a central angle of 120 degrees. As shown in FIG. 16, the B filter portion 120a transmits B light in the blue band (380 to 500 nm) out of the broadband light BB. The G filter portion 120b transmits G light in the green band (450 to 630 nm) out of the broadband light BB. The R filter portion 120c transmits R light in the red band (580 to 760 nm) out of the broadband light BB. The B light, the G light, and the R light passes through the rotation filter 112 sequentially in accordance with the rotation of the rotation filer 112. The B light, the G light, and the R light is incident on the light guides 28 and 29 through a condenser lens 116 and an optical fiber 117.

The second filter area 121 is provided with a BN filter portion 121a, a G filter portion 121b, and an R filter portion 121c, each in a shape of an annular sector with a central angle of 120 degrees. The optical transmission characteristics of the G filter portion 121b are similar to those of the G filter portion 120b. The optical transmission characteristics of the R filter portion 121c are similar to those of the R filter portion 120c. As shown in FIG. 16, the BN filter portion 121a transmits blue narrowband light BN in a wavelength range of 450 to 500 nm out of the broadband light BB. Similar to the G filter portion 120b, the G filter portion 121b transmits the G light in a green band (450 to 630 nm). Similar to the R filter portion 120c, the R filter portion 121c transmits the R light in a red band (580 to 760 nm). Thereby, the BN light, the G light, and the R light passes through the rotation filter 112 sequentially in accordance with the rotation of the rotation filer 112. The BN light, the G light, and the R light is incident on the light guides 28 and 29 through the condenser lens 116 and the optical fiber 117.

Figure 17A:
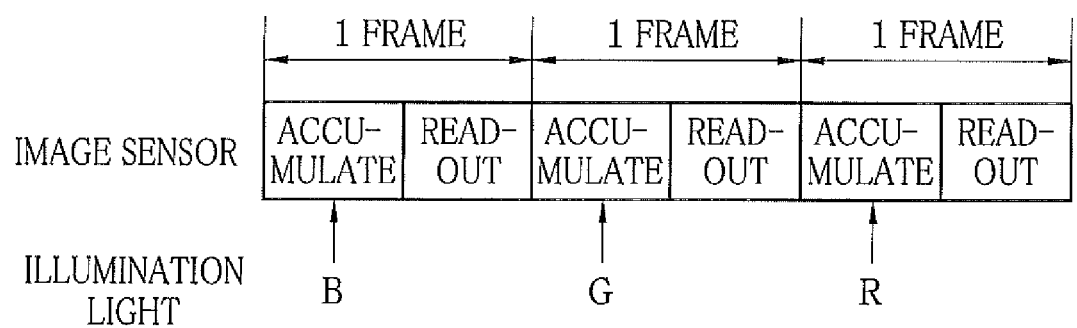
FIG. 17A is an explanatory view describing imaging control in a normal mode of another embodiment.

Because the endoscope system 100 employs the rotation filter method, the imaging control in the endoscope system 100 is different from that in the endoscope system 10. In the normal mode, as shown in FIG. 17A, the B light, the G light, and the R light is emitted sequentially with a single rotation of the rotation filter. Meanwhile, the color image sensor 60 sequentially images the region of interest and outputs frame-sequential image signals (a blue signal, a green signal, and a red signal for illumination light of each color, in total of 9 color signals in three frames). This procedure is repeated in the normal mode. The normal light image, which is an image obtained with the illumination of the white light, is produced based on the blue signal corresponding to the B light, the green signal corresponding to the G light, and the red signal corresponding to the R light out of the frame-sequential image signals outputted.

Figure 17B:
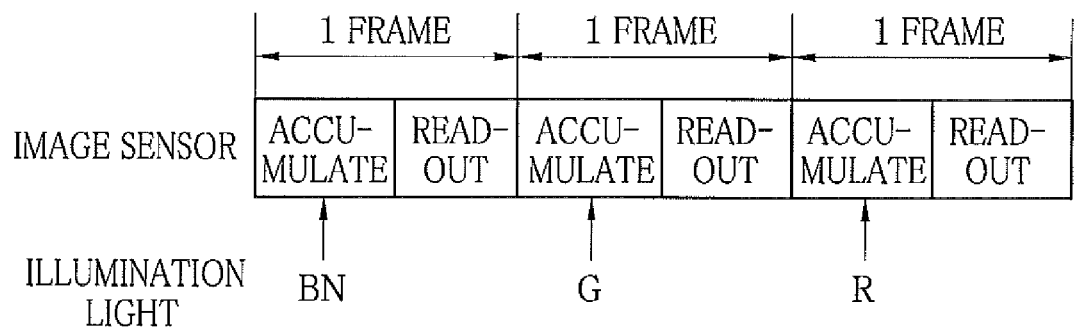
FIG. 17B is an explanatory view describing imaging control in an oxygen saturation mode of another embodiment.

In the oxygen saturation mode, as shown in FIG. 17B, image light of the BN light, image light of the G light, and image light of the R light is captured sequentially in three respective frames with the color image sensor 60, and the frame-sequential image signals are outputted accordingly. This procedure is repeated in the oxygen saturation mode. Note that, in the first frame, a blue signal, a green signal, and a red signal, acquired by imaging with the illumination of the BN light, are denoted as b1, g1, and r1, respectively. In the second frame, a blue signal, a green signal, and a red signal, acquired by imaging with the illumination of the G light, are denoted as b2, g2, and r2, respectively. In the third frame, a blue signal, a green signal, and a red signal, acquired by imaging with the illumination of the R light, are denoted as b3, g3, and r3, respectively.

Unlike the above embodiments, the endoscope system 100 uses the blue signal b1 of the first frame, the green signal g2 of the second frame, and the red signal r3 of the third frame to calculate the oxygen saturation level. Before calculating the oxygen saturation level using the signals b1, g2, and r3, a registration process is performed. In the registration process, an image composed of the blue signal b1 and an image composed of the red signal r3 are aligned with an image composed of the green signal g2. Note that the wavelength component (450 to 500 nm) in the blue signal b1 is different from the wavelength component (center wavelength of 473 nm) in the blue signal B1 shown in FIG. 6. However, in each of the wavelength components, the absorption coefficient of the oxyhemoglobin is higher than that of the deoxyhemoglobin. Hence the difference between the wavelength components does not affect the calculation of oxygen saturation level.

In the registration process, as shown in FIG. 18, a first shift amount between the first and second frames and a second shift amount between the second and third frames are calculated. The first shift amount is an amount of shift between an image composed of the green signal g1 and an image composed of the green signal g2, which are similar in signal characteristics and image structure. To calculate the first shift amount, the method for calculating the shift amount, described in the above embodiments, is used. Thereby, the shift amount $\Delta F1x$ in the X direction and a shift amount $\Delta F1y$ in the Y direction are calculated between the image composed of the green signal g1 and the image composed of the green signal g2. The second shift amount is an amount of shift between an image composed of the red signal r2 and an image composed of the red signal r3, which are similar in signal characteristics and image structure. The method for calculating the shift amount, described in the above embodiments, is used to calculate the second shift amount. Thereby, the shift amount ΔF2x in the X direction and a shift amount ΔF2y in the Y direction are calculated between the image composed of the red signal r2 and the image composed of the red signal r3.

Figure 19:
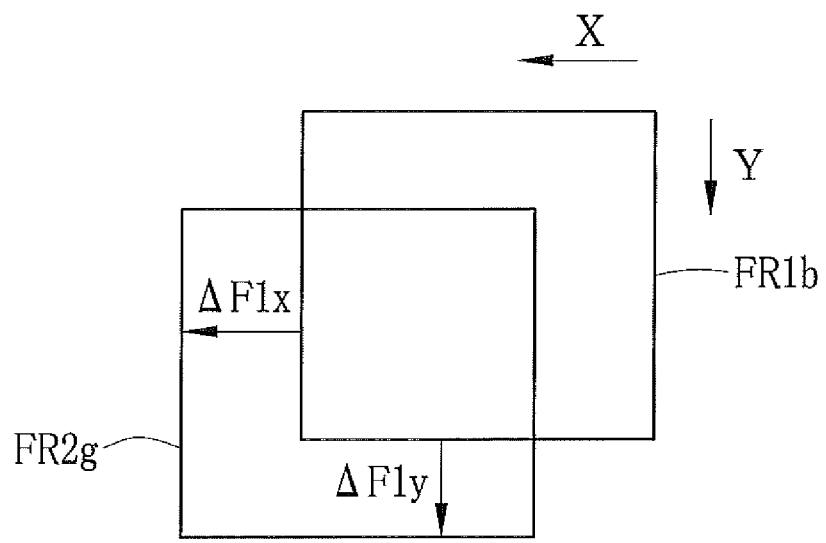
FIG. 19 is an explanatory view illustrating registration of a blue image FR1$b$ and a green image FR2$g$.
Figure 20:
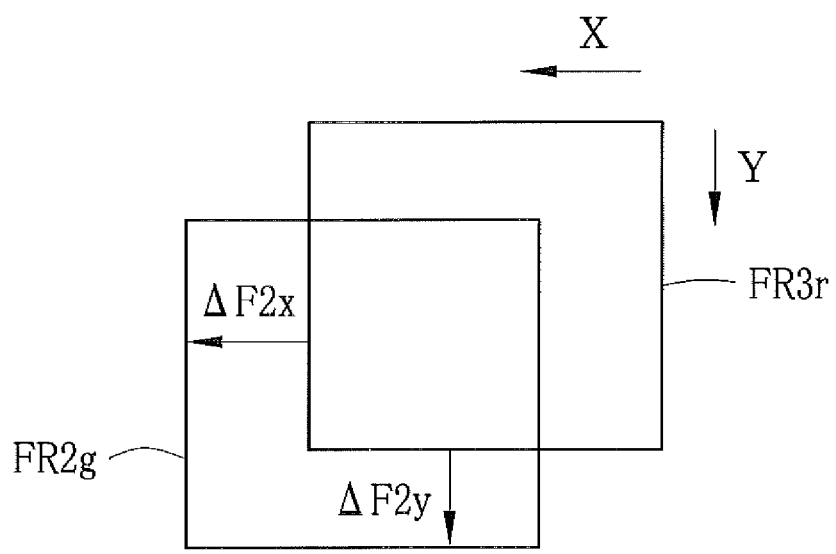
FIG. 20 is an explanatory view illustrating registration of a red image FR3$r$ and a green image FR2$g$.

After each of the first and second shift amounts between the images of the respective frames are calculated, as shown in FIG. 19, the image Fr1b composed of the blue signal b1 of the first frame is moved by the first shift amount (ΔF1x, ΔF1y) in a direction to cancel out the shift between the first and second frames. Thereby, the shift between the image FR1b composed of the blue signal b1 of the first frame and the image FR2g composed of the green signal g2 of the second frame is canceled out, and thus the corresponding pixels in the images FR1b and FR2g are aligned with each other. As shown in FIG. 20, an image FR3r composed of the red signal r3 of the third frame is moved by the second shift amount (ΔF2x, ΔF2y) in a direction to cancel out the shift between the second and third frames. Thereby, the shift between the image FR2g composed of the green signal g2 of the second frame and the image FR3r composed of the red signal r3 of the third frame is canceled out. Thus, the images FR1b, FR2g, and FR3r are aligned or registered with each other.

After the registration of the images, the oxygen saturation level is calculated based on the blue signal b1, the green signal g2, and the red signal r3. Because the three images (FR1b, FR2g, and FR3r) are aligned with each other, the oxygen saturation level in each pixel is calculated accurately. The oxygen saturation level is calculated in a manner similar to the above embodiments. Note that the signal ratio b1/g2 corresponds to the signal ratio B1/G2 of the above embodiments. The signal ratio r3/g2 corresponds to the signal ratio R2/G2 of the above embodiments. The correlation storage 85 stores the correlation among the signal ratios b1/g2 and r3/g2 and the oxygen saturation level.

Note that the oxygen saturation level is imaged in the above embodiments. Alternatively or in addition, oxyhemoglobin index or deoxyhemoglobin index may be imaged. The oxyhemoglobin index is calculated using an expression "blood volume (sum of oxyhemoglobin and deoxyhemoglobin)× oxygen saturation level (%)". The deoxyhemoglobin index is calculated using an expression "blood volume×(100-oxygen saturation level) (%)".

Various changes and modifications are possible in the present invention and may be understood to be within the present invention.

Note that, in the above embodiments, the color image sensor has the pixels of additive primary colors (B, G, and R) arranged in a matrix. Instead, an array of pixels of subtractive primary colors (Y, M, and C) may be used. Four or more types of pixels including, for example, a monochrome type may be used.

What is claimed is:

1. An endoscope system comprising:
   a lighting section for applying at least first illumination light and second illumination light, in respective frames, to a region of interest, a wavelength range of the first illumination light being different from a wavelength range of the second illumination light, the region of interest including a blood vessel;
   an image signal acquisition section having a color image sensor with an array of pixels of at least three primary colors, the image signal acquisition section imaging the region of interest in the each frame, the image signal acquisition section imaging the region of interest illuminated with the first illumination light to acquire a blue signal, a green signal and a red signal of a first frame, the image signal acquisition section imaging the region of interest illuminated with the second illumination light to acquire a blue signal, a green signal and a red signal of a second frame;
   a shift amount calculator for calculating a shift amount between an image of the first frame and an image of the second frame based on the signals of same color;
   a registration section for aligning images of the blue signal of the first frame and the green and red signals of the second frame, used for calculating an oxygen saturation level of hemoglobin in blood, based on the shift amount;
   an oxygen saturation image generator for producing an oxygen saturation image of the oxygen saturation level based on only the blue signal of the first frame, and the green and red signals of the second frame that are aligned; and
   a display section for displaying the oxygen saturation image.

2. The endoscope system of claim 1, wherein each of the first and second illumination light is white light, and the shift amount calculator calculates the shift amount between the green images produced based on the green signals.

3. The endoscope system of claim 2, wherein the registration section moves the blue signal of the first frame to be aligned with the green and red signals of the second frame.

4. The endoscope system of claim 2, wherein the first and second illumination light is produced by wavelength conversion of respective narrowband light, having different wavelength ranges, with a wavelength converter.

5. The endoscope system of claim 4, wherein the each narrowband light is laser beams.

6. The endoscope system of claim 5, wherein the center wavelengths of the laser beams are 473 nm and 445 nm, respectively.

7. The endoscope system of claim 1, wherein the lighting section applies the first illumination light, the second illumination light, and a third illumination light, in respective frames, to the region of interest, and a wavelength range of the third illumination light is different from the wavelength range of each of the first and second illumination light, and the image signal acquisition section images the region of interest in the each frame, and the image signal acquisition section images the region of interest illuminated with the first illumination light to acquire the three color signals of the first frame, and the image signal acquisition section images the region of interest illuminated with the second illumination light to acquire the three color signals of the second frame, and the image signal acquisition section images the region of interest illuminated with the third illumination light to acquire three color signals of a third frame, and the shift amount calculator calculates a first shift amount between images of the color signals of same color of the first and second frames and a second shift amount between images of the color signals of same color of the second and third frames, and the registration section aligns images of predetermined color signals, used for calculating the oxygen saturation level, out of the color signals of the first, second, and third frames based on the first and second shift amounts.

8. A processor for an endoscope system, the endoscope system comprising a lighting device and an endoscope device, the lighting device applying at least first and second illumination light, in respective frames, to a region of interest including a blood vessel, a wavelength range of the first illumination light being different from a wavelength range of the second illumination light, the endoscope device imaging the region of interest in the each frame with a color image sensor having an array of pixels of at least three primary colors, the endoscope device imaging the region of interest illuminated with the first illumination light to acquire a blue signal, a green signal and a red signal of a first frame, the endoscope device imaging the region of interest illuminated with the second illumination light to acquire a blue signal, a green signal and a red signal of a second frame, the processor, executing computer executable instructions stored in a non-transitory computer readable medium, configured to perform functions of:

receiving the color signals of each of the first and second frames from the endoscope device;

calculating a shift amount between an image of the first frame and an image of the second frame based on the signals of the same color;

aligning images of the blue signal of the first frame and the green and red signals of the second frame, used for calculating an oxygen saturation level of hemoglobin in blood, based on the shift amount; and producing an oxygen saturation image of the oxygen saturation level based on only the blue signal of the first frame, and the green and red signals of the second frame that are aligned.

9. An image producing method comprising the steps of:

applying at least first illumination light and second illumination light having different wavelength ranges, in respective frames, to a region of interest including a blood vessel, and imaging the region of interest in the each frame with a color image sensor having an array of pixels of at least three primary colors, the color image sensor imaging the region of interest illuminated with the first illumination light to acquire a blue signal, a green signal and a red signal of a first frame, the color image sensor imaging the region of interest illuminated with the second illumination light to acquire a blue signal, a green signal and a red signal of a second frame;

calculating a shift amount between an image of the first frame and an image of the second frame based on the color signals of same color;

aligning images of the blue signal of the first frame and the green and red signals of the second frame, used for calculating an oxygen saturation level of hemoglobin in blood, based on the shift amount; and producing an oxygen saturation image of the oxygen saturation level based on only the blue signal of the first frame, and the green and red signals of the second frame that are aligned.

10. The endoscope system of claim 1, further comprising:

a signal ratio calculator for calculating a signal ratio between corresponding pixels in a blue image of the first frame and a green image of the second frame, and a signal ratio between corresponding pixels in a red image of the second frame and a green image of the second frame;

a correlation storage for storing the correlation among the signal ratios and the oxygen saturation level; and an oxygen saturation calculator for calculating an oxygen saturation level in each pixel with the use of the correlation stored in the correlation storage and the signal ratios calculated by the signal ratio calculator.

* * * * *